(12) United States Patent
Hwu et al.

(10) Patent No.: US 8,828,975 B2
(45) Date of Patent: *Sep. 9, 2014

(54) PHOSPHATE-CONTAINING NANOPARTICLE DELIVERY VEHICLE

(75) Inventors: Jih Ru Hwu, Hsinchu (TW); Yu-Sern Lin, Hsinchu (TW); Chen-Sheng Yeh, Hsinchu (TW); Dar-Bin Shieh, Tainan (TW); Wu-Chou Su, Tainan (TW)

(73) Assignee: National Cheng-Kung University, Tainan (TW)

( * ) Notice: Subject to any disclaimer, the term of this patent is extended or adjusted under 35 U.S.C. 154(b) by 79 days.

This patent is subject to a terminal disclaimer.

(21) Appl. No.: 13/548,972

(22) Filed: Jul. 13, 2012

(65) Prior Publication Data

US 2012/0289712 A1 Nov. 15, 2012

Related U.S. Application Data

(63) Continuation-in-part of application No. 12/686,996, filed on Jan. 13, 2010, now abandoned.

(30) Foreign Application Priority Data

Sep. 25, 2009 (TW) .............................. 98132497 A

(51) Int. Cl.

| | | |
|---|---|---|
| *C07D 493/00* | (2006.01) | |
| *A61K 38/00* | (2006.01) | |
| *A61K 9/16* | (2006.01) | |
| *A61K 31/665* | (2006.01) | |
| *C07F 9/6558* | (2006.01) | |
| *C07F 9/655* | (2006.01) | |
| *A61K 47/48* | (2006.01) | |

(52) U.S. Cl.
CPC ........... *C07F 9/65512* (2013.01); *A61K 31/665* (2013.01); *C07F 9/65586* (2013.01); *A61K 47/48861* (2013.01)
USPC ............ 514/100; 549/511; 549/212; 549/510

(58) Field of Classification Search
CPC ............ C07F 9/65512; C07F 9/65586; A61K 31/665; A61K 47/48861
USPC .......................... 549/510, 511, 212; 514/100
See application file for complete search history.

(56) References Cited

U.S. PATENT DOCUMENTS

| 7,250,499 B2 | 7/2007 | Mirkin et al. |
| 7,329,638 B2 | 2/2008 | Yang et al. |
| 2005/0271593 A1 | 12/2005 | Yeh et al. |

FOREIGN PATENT DOCUMENTS

DE    10 2004 035 803 A1    3/2005

OTHER PUBLICATIONS

Hwu et al., "Targeted Paclitaxel by Conjugation to Iron Oxide and Gold Nanoparticles," J. Am. Chem. Soc. 2009, 131, pp. 66-68. Published on Internet Dec. 10, 2008.
Li et al., "The Enhancement Effect of Gold Nanoparticles in Drug Delivery and as Biomarkers of Drug-Resistant Cancer Cells," ChemMedChem 2007, 2, pp. 374-378.

*Primary Examiner* — Andrew D Kosar
*Assistant Examiner* — Raymond Covington
(74) *Attorney, Agent, or Firm* — Muncy, Geissler, Olds & Lowe, P.C.

(57) ABSTRACT

A phosphate-containing nanoparticle delivery vehicle includes a nanoparticle, an active ingredient, and a phosphodiester moiety connecting the nanoparticle and the active ingredient and forms a prodrug. The nanoparticle delivery vehicle achieves the function of increasing hydrophilicity of the active ingredient and specificity against tumor cells. Advantages of the nanoparticle material include biocompatibility, magnetism and/or controllable drug release.

13 Claims, 5 Drawing Sheets

PHOSPHATE-CONTAINING NANOPARTICLE DELIVERY VEHICLE

RELATED APPLICATIONS

This application is a Continuation-in-part of application Ser. No. 12/686,996 filed on Jan. 13, 2010 now abandoned.

BACKGROUND OF THE INVENTION

1. Field of the Invention

The present invention relates to a nanoparticle delivery vehicle, more particularly to a nanoparticle delivery vehicle having a phosphate moiety.

2. Description of the Prior Art

Selective targeting of cancer cells has limited success by application of modern chemotherapeutic methods. Paclitaxel (i.e., Taxol) is one of the most popular chemotherapeutic agents used nowadays for treatment of breast, ovarian, and lung cancers. Being able to promote tubulin assembly into microtubules, paclitaxel brings significant impact mainly because of its mechanism of action. On the other hand, its drawbacks come from the lack of tumor specificity and low solubility in water.

For improving the tumor specificity and low water solubility issues of anticancer drugs, Pero et al. (US. Patent Application No. 20030109500) administered a sufficient amount of a cytotoxic agent formulated into a phosphate prodrug form having substrate specificity for microvessel phosphatases. Microvessels therefore are destroyed preferentially over other normal tissues because the less cytotoxic prodrug form is converted to the highly cytotoxic dephosphorylated form.

However, it may not be sufficient for highly hydrophobic anticancer drugs to improve their hydrophilicity with single phosphate moiety, and the hydrophilicity issue still needs to be solved. Furthermore, the above-mentioned technique may not precisely deliver anticancer drugs to the position of cancer cells and may not be able to selectively target cancer cells in vivo.

To sum up, it is now a current goal to develop a novel drug delivery vehicle for improving the hydrophilicity of anticancer drugs and precisely delivering to the position of cancer cells.

SUMMARY OF THE INVENTION

The present invention is directed to provide a nanoparticle delivery vehicle, which may achieve the function of increasing hydrophilicity of the active compound and specificity against tumor cells and provides advantages of the nanoparticle material, such as biocompatibility, magnetism and/or controllable drug release.

A phosphate-containing nanoparticle delivery vehicle of the formula:

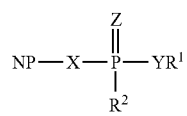

wherein NP is a nanoparticle; $R^1$ is an anticancer drug molecule; $R^2$ is a member selected from the group consisting of OH, halogen, C1-C5 alkoxy group; each of X, Y is a member selected from the group consisting of NH, O and S; and Z is a member selected from the group consisting of O and S.

Other advantages of the present invention will become apparent from the following descriptions taken in conjunction with the accompanying drawings wherein are set forth, by way of illustration and example, certain embodiments of the present invention.

BRIEF DESCRIPTION OF THE DRAWINGS

The foregoing aspects and many of the accompanying advantages of this invention will become more readily appreciated as the same becomes better understood by reference to the following detailed descriptions, when taken in conjunction with the accompanying drawings, wherein.

DESCRIPTION OF THE PREFERRED EMBODIMENT

Figure 1A:
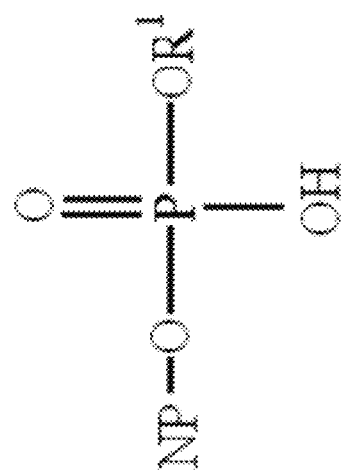
FIG. 1a is a chemical formula illustrating a nanoparticle delivery vehicle according to an embodiment of the present invention.

A nanoparticle delivery vehicle of the present invention includes a phosphodiester moiety connecting a nanoparticle and an active ingredient to form a prodrug. The nanoparticle delivery vehicle achieves the function of increasing hydrophilicity of the active ingredient and specificity against tumor cells. Advantages of the nanoparticle material may include biocompatibility, magnetism and/or controllable drug release. The design for the nanoparticle delivery vehicle of the present invention is described in detail as followings.

Selecting and Modifying Nanoparticles:

There are no limits on the physical parameters of a nanoparticle component of the present invention. The design of a delivery vehicle may, however, take into account the biocompatibility of the nanoparticle delivery vehicle, where appropriate. The physical parameters of a nanoparticle delivery vehicle can be optimized, with the desired effect governing the choice of size, shape and material. Since the delivery vehicle of the present invention would be used for carrying an active ingredient, e.g. a drug, in vivo, the biocompatibility thereof may be taken into consideration.

Among a diverse selection of nanoparticles, any of those with magnetization, e.g. iron, cobalt, nickel and oxides thereof, may be chosen as the delivery vehicle for being detectable and tractable. Among nanoparticles with magnetization, iron oxide nanoparticles, Fe-NPs, inherently exhibits strong magnetization and little to no toxicity in vivo, and hence are preferred over the others. In the clinical field of human medicine, these particles are used as delivery vehicles for drugs, genes, and radionuclides. When used to form ferrofluid, these nanoparticles can be tracked for the purpose of contrast agents. When an external magnetic field is applied, these superparamagnetic Fe-NPs are allowed to be delivered to the desired target area and be fixed at a specific site while the medication is released and acts locally.

Functionalized gold nanoparticles, Au-NPs, are promising candidates for drug delivery because of their unique dimensions, tunable functionalities on the surface, and controllable drug release. Wang et al. (ChemMedChem, 2007, 2, 374-378) have revealed the application of 3-mercaptopropionic acid capped Au-NPs in drug delivery and as biomarkers of drug-resistant cancer cells.

Other biocompatible nanoparticles may also be chosen as the delivery vehicle of the present invention, containing without limitations to titanium dioxide, zinc oxide, tin dioxide, copper, aluminum, cadmium selenide, silicon dioxide or diamond.

The nanoparticle delivery vehicle of the present invention may be further modified for desired properties. In one embodiment, the nanoparticle delivery vehicle of the present invention may be chemically modified for improved hydrophilicity. For example, these nanoparticles may be provided with poly-$NH_3^+$ for improved hydrophilicity, and the preparation thereof is referred in Yeh et al., titled "Replace With Method for Preparation of Water-soluble and Dispersed Iron Oxide Nanoparticles and Application Thereof"; Germany Patent 102004035803, 2007.

In addition, these nanoparticles may be modified for increasing their biocompatibility as well as penetrating cell membranes. In one example, the nanoparticles may be provided with hydrophilic polyethylene glycols, PEGs, for achieving the above mechanism, and the preparation method would be later detailed.

Role of Phosphodiester Moiety

Chemotherapeutic agents possessing a phosphate unit would preferentially interact with the cancer cells. Moreover, dephosphorylation often takes place more easily in cancer cells than in normal cells. An advantage of our design to incorporate the phosphodiester moiety in active ingredient-containing nanoparticles is the capability of selective targeting. Hydrolysis of the phosphodiester moieties with the aid of phosphodiesterase could free active ingredients from nanoparticles.

FIG. 1a is a schematic diagram illustrating a formula of the present invention, wherein the NP represents a nanoparticle, $R^1$ represents an active ingredient, and NP and $R^1$ are coupled with a phosphodiester moiety.

Figure 1B:
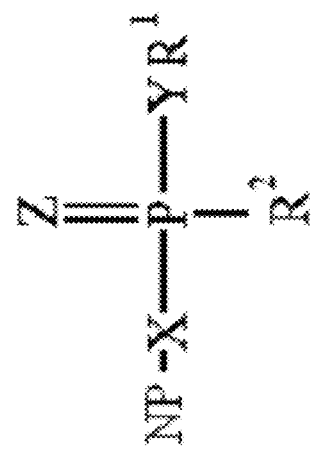
FIG. 1b is a chemical formula illustrating a nanoparticle delivery vehicle according to an embodiment of the present invention.

Referring to FIG. 1b for another formula of the present invention, the phosphodiester moiety may be modified or substituted, wherein the $R^2$ may be OH, halogen, C1-C5 alkoxy group, X, Y may be NH, O or S, and Z may be O or S.

Selecting an Active Ingredient

The active ingredient may be a drug molecule, a biological macromolecule or a polymer. As mentioned above, chemotherapeutic agents possessing a phosphate unit would preferentially interact with the cancer cells. Moreover, dephosphorylation often takes place more easily in cancer cells than in normal cells. Therefore, a preferred example of the present invention may be an anticancer drug molecule. The anticancer drug molecule may include a signal transduction inhibitor, a protease inhibitor, an antidiabetic drug, an actin inhibitor or an antimetabolite.

Inhibitors of signal transduction pathways have been used to treat cancer resulted in reduced proliferation of cells is and/or enhanced apoptosis of tumor cells since aberrant signal transduction can lead to malignant transformation, growth, and progression. A number of signal transduction inhibitors (STIs) have been developed and their ability to suppress tumor growth is currently under investigation. STIs may be used for targeting receptors and/or kinase belonging to a tyrosine kinase of a platelet derived growth factor (PDGF) receptor family, an EGF receptor kinase family, an ABL kinase family, a VEGF kinase family or an src kinase family. Signal transduction inhibitors of the present invention include, but are not limited to, (1) insulin-like growth factor-1 (IGF-1) and insulin receptor tyrosine kinase inhibitors such as AG 1024;
(2) epidermal growth factor (EGF) receptor inhibitors such as Iressa;
(3) mTOR (mammalian target of rapamycin) inhibitors such as Everolimus and Temsirolimus;
(4) MEK/MAPK inhibitor such as U0126;
(5) cyclin-dependent kinase inhibitors such as flavopiridol;
(6) phosphatidyl inositol kinase inhibitors such as LY294002;
(7) bcr/abl kinase inhibitors such as Gleevec; and
(8) JAK-2 tyrosine kinase inhibitor such as AG-490.

Protease inhibitors, for example, are inhibitors to MMP (matrix metalloproteases) which are formed to an increased extent, or are activated, in association with diseases such as rheumatoid arthritis or cancer, thereby leading to excessive tissue breakdown, to new blood vessels and to metastases. Target enzymes involved are, in particular, MMP-2, MMP-3 and MMP-9, as proteases, in the abovementioned pathological processes. The MMP inhibitors may include Marimastat, tetracyclines, Prinomastat, doxycycline or minocycline.

Examples of antidiabetic drugs used for anticancer purpose may include Metformine or Phenformin. Examples of actin inhibitors may include cytochalasin B, cytochalasin D, cytochalasin A, cytochalasin E, latrunculin or Phalloidin. Examples of cytotoxic antibiotics may include actinomycin, doxorubicin, daunorubicin, valrubicin or idarubicin. Examples of topoisomerase inhibitors may include irinotecan, topotecan, amsacrine, etoposide or teniposide. Antimetabolites may include 6-Mercaptopurine (6-MP), Azathioprine (AZA), Methotrexate, 6-thioguanine (6-TG), thioguanine, 6-thioinosine or thiouridine.

In one preferred example, the drug molecule may include OH moiety for forming a phosphodiester bond. Examples of an anticancer drug having a hydroxyl group include paclitaxel, Cytarabine (Ara C), Fludarabine (Fludara®), Capecitabine (Xeloda®), Docetaxel, Epirubicin, and Doxorubicin.

In addition, small molecule drugs may include $NH_2$ or SH group for forming phosphodiester bond. An anticancer drug having an amine group may be 6-Mercaptopurine (6-MP), Azathioprine (AZA), Metformin, Phenformin or Methotrexate. An anticancer drug including thiol group may be thiopurines such as 6-thioguanine (6-TG), thioguanine, Mercaptopurine (6-MP) and 6-thioinosine and thiouridine.

Biological macromolecules, containing without limitations to nucleic acid, nucleotide, oligonucleotide, peptide and protein, may form phosphodiester bond for delivery vehicle via their hydroxyl groups or so on.

The following descriptions of specific embodiments of the present invention have been presented for purposes of illustrations and description, and they are not intended to be exclusive or to limit the present invention to the precise forms disclosed.

EXAMPLE 1

Paclitaxel-Fe-NP Preparation

Figure 2:
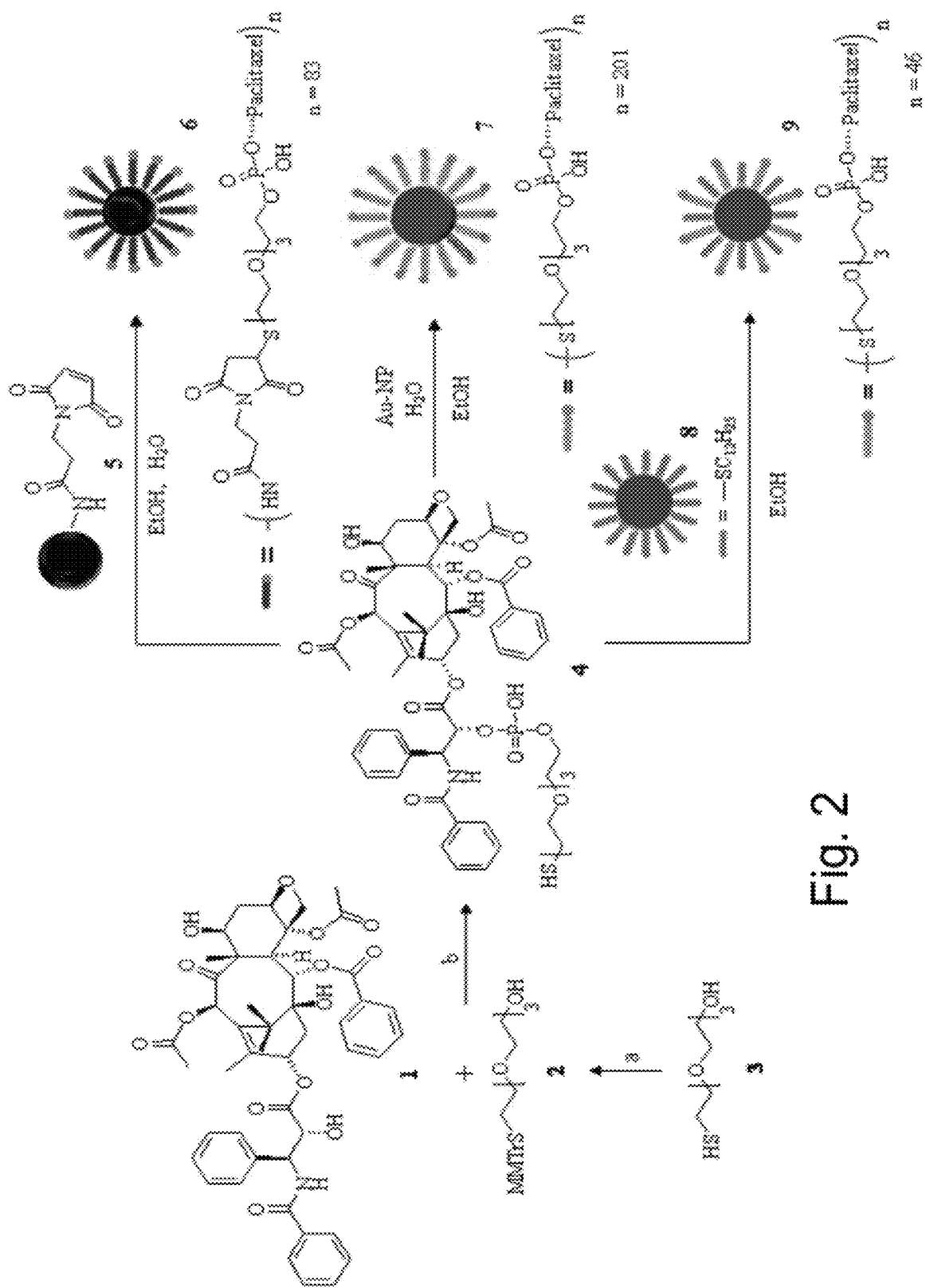
FIG. 2 is a schematic diagram illustrating the preparation of nanoparticle delivery vehicles according to an embodiment of the present invention.

In one specific example of the present invention, the nanoparticle is made of ferric oxide, which has magnetization and biocompatibility; and the active ingredient is paclitaxel. FIG. 2 is a schematic diagram illustrating paclitaxel-conjugated nanoparticles of the present invention. First, the thiol terminal of tetraethylene glycol monothiol (3) was protected with a stoichiometric amount of (mono-4-methoxy)trityl chloride (MMTrCl) in the presence of triethyl amine to give (monomethoxy)tritylated thiol 2 in 65% yield. Then paclitaxel (1) was treated with (MeO)PCl$_2$ (1.54 equiv) and collidine in THF, (monomethoxy)tritylated thiol 2 (1.0 equiv), I$_2$ (2.0 equiv), and water in sequence to provide the desired pro-paclitaxel 4 as the major product in 72% yield.

The "one-flask method" in the conversion of 1+2→4 allowed three steps accomplished in situ: coupling of the paclitaxel with the PEG-SH spacer, oxidation of the phosphite center, and deprotection of the (monomethoxy)trityl group. The "one-flask method" is described in detail in Hwu, J. R et. al. (Bioorg. Med. Chem. Lett. 1997, 7, 545-548), the entire contents of which are incorporated by reference herein.

Second, we modified the ammonium groups in Fe$_3$O$_4$-nanoparticles [Fe-NP-(NH$_3$)+n] by using N-succinimidyl 3-(N-maleimido)propionate (1.2 equiv) in DMSO to produce the functionalized Fe-NP 5. The water-soluble and dispersed Fe$_3$O$_4$-nanoparticles 5 were prepared from two solutions containing Fe$^{II}$ and Fe$^{III}$ as well as an organic acid containing an amino group. Then the pH of the solution was adjusted, and the proper amount of adherent was added to achieve complete coating of the particle surface with —NH$_3^+$ groups.

Third, attachment of thiol 4 (4.3 equiv) to Fe-NP 5 in methanol at room temperature produced the desired Michael adduct paclitaxel-Fe-NP 6, of which the mean diameter was 6.1±0.8 nm as determined by TEM.

Figure 3:
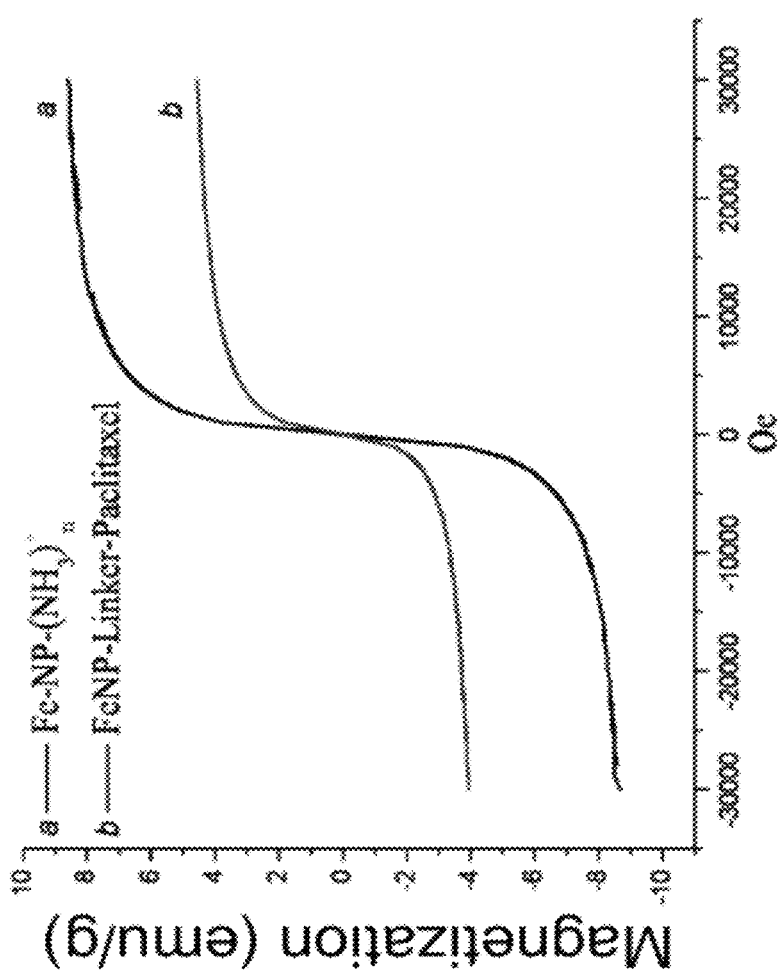
FIG. 3 is a line chart illustrating the results of the nanoparticle delivery vehicles of the present invention.

Before and after conjugation, the magnetization loops of Fe-NP-(NH$_3$)$^+_n$ 5 and paclitaxel-Fe-NP 6 were measured at room temperature; their curves are shown in FIG. 3. The saturation magnetization for paclitaxel-Fe-NP 6 was determined as 4.0 emu/mg, which indicates its magnetic detectability and the tracking feasibility.

On the other hand, our results from thermogravimetric analysis (TGA) of hybrid nanoparticles 5 and 6 reveal that the estimated average number of succinimido linkers and paclitaxel attached on the iron oxide cores were 92 and 83, respectively.

EXAMPLE 2

Hydrophilic Paclitaxel-Au-NP Preparation

Furthermore, we incorporated pro-paclitaxel 4 (500-1000 equiv) through its thiol terminal onto colloidal Au-NPs in water at room temperature, which was prepared by reduction of HAuCl$_4$ with sodium citrate.

The desired hydrophilic paclitaxel-Au-NP 7 was obtained as indicated by a 19 nm hyperchromic and bathochromic shift of UV/visible peak. The paclitaxel-Au-NP 7 contained 201 functional paclitaxel sites on average as determined by the TGA method. The TEM micrographs in FIG. 4b indicates that the paclitaxel-Au-NPs 7 have a diameter of 14.6±0.7 nm were well dispersed.

EXAMPLE 3

Hydrophobic Paclitaxel-Au-NP Preparation

While the conjugated paclitaxel-Au-NP 7 possesses good hydrophilicity, the present invention attempted to obtain hydrophobic paclitaxel-conjugated Au-NPs 9.

Figures 4A, 4B, 4C:
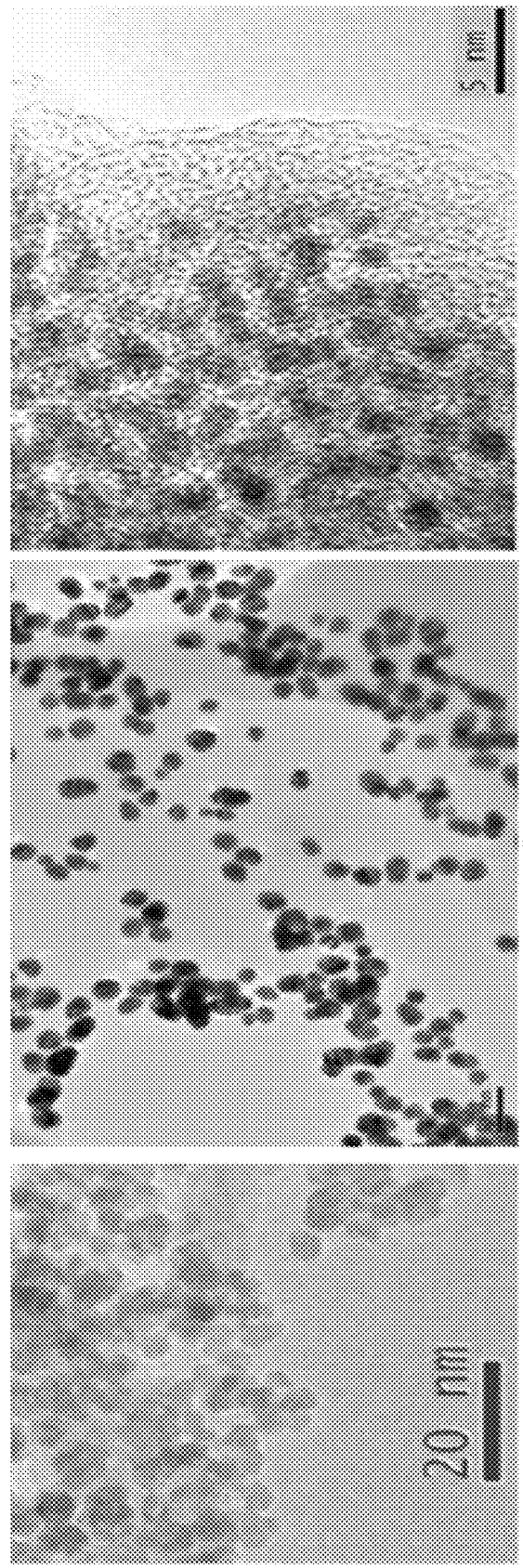
FIGS. 4a to 4c are pictures illustrating the results of the nanoparticle delivery vehicles of the present invention.

Accordingly dodecanethiol ligands in the clusters 8 were exchanged with paclitaxel-containing thiol 4 in toluene at room temperature for 120 h. The dispersed hybrid paclitaxel-conjugated Au-NPs 9, as shown in FIG. 4c, were generated with an average diameter of 2.1±0.3 nm. We determined the average number of the paclitaxel molecules bound on each Au-NP 9 as 46 by the displacement method involving the use of mercaptoethanol.

Hydrophilicity and Biocompatibility Test

The paclitaxel-conjugated nanoparticles 6 and 7 exhibited good hydrophilicity, of which dispersion was 312 and 288 µg/mL, respectively. In comparison with the parent paclitaxel molecule (0.4 µg/mL), their hydrophilicity was increased 780 and 720 times. In comparison with PEG-paclitaxel 4 (3.26 µg/mL), their hydrophilicity was increased 96 and 88 times.

Because the PEG linker possesses good water solubility and Fe-NP-(NH$_3$)$^+_n$ is miscible with water, the improvement in hydrophilicity of paclitaxel-Fe-NP 6 should be attributed to both the PEG spacers and the Fe-NP-(NH$_3$)$^+_n$ species. Our use of the flexible PEG spacer may also offer advantages to aid prodrugs 6 and 7 in penetrating cell membranes as well as to increase their biocompatibility.

Drug Release Test

Chemotherapeutic agents possessing a phosphate unit would preferentially interact with the cancer cells. Moreover, dephosphorylation often takes place more easily in cancer cells than in normal cells. An advantage of our design to incorporate of the phosphodiester moiety in paclitaxel-containing nanoparticles is their capability of selective targeting. Hydrolysis of the phosphodiester moieties with the aid of phosphodiesterase could liberate free paclitaxel from nanoparticles.

Figure 5:
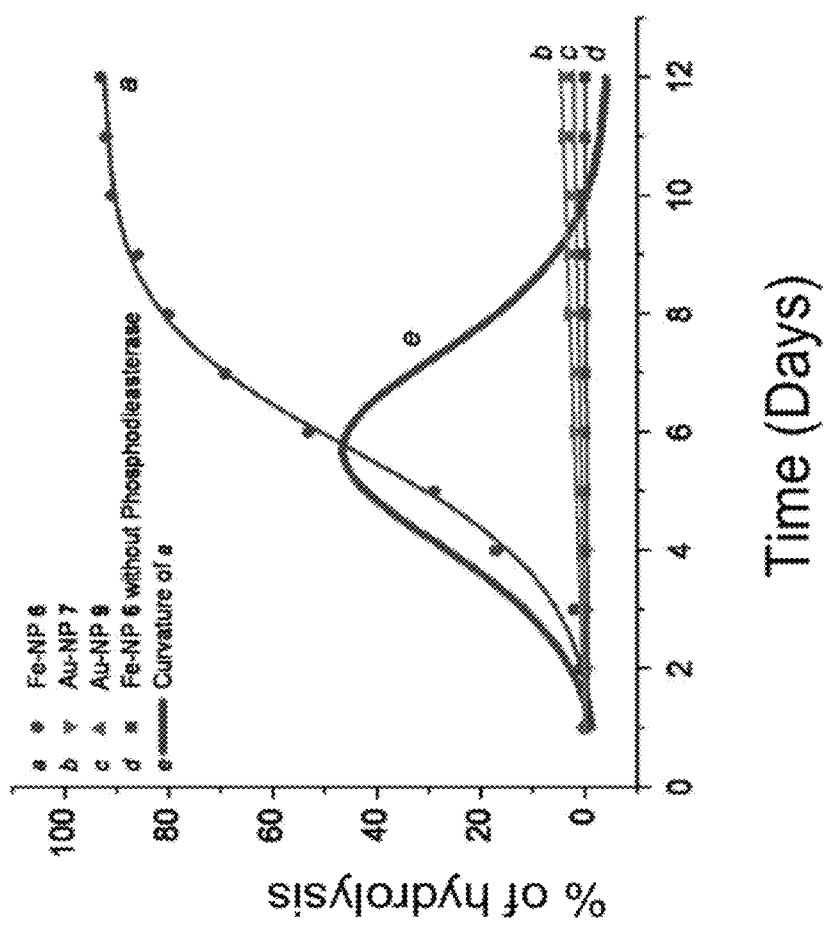
FIG. 5 is a line chart illustrating the results of the nanoparticle delivery vehicles of the present invention.

The feasibility of this hypothesis was confirmed by our experiments, in which up to 91% of paclitaxel-containing ligand in paclitaxel-Fe-NP 6 (prodrug) were hydrolyzed by phosphodiesterase after 10 days to give free paclitaxel molecules as detected by HPLC (see FIG. 5, curve a). Paclitaxel-Fe-NP 6 therefore acts as a "biofunctional material".

Cytotoxicity Test for Cancer Cells

Furthermore, the present invention performed an efficacy evaluation of the pro-drug paclitaxel-Fe-NP 6 on human cancer cells (OECM1) and human normal cells (HUVEC) by the MTT assay. The results showed significant (i.e., 10$^4$) enhancement of cytotoxicity resulting from the pro-drug to cancer cells in comparison with normal cells within 6 days. Their IC$_{50}$ values were 5.03×10$^{-7}$ and 3.58×10$^{-3}$ µg/mL, respectively. Moreover, there is no significant detected amount (i.e., <0.50%) of free paclitaxel 1 from paclitaxel-Fe-NP 6 in FCS (calf serum, 2.50×10$^{-4}$ M) after 12 days.

To sum up, the nanoparticle delivery vehicle of the present invention includes a nanoparticle by using Fe$_3$O$_4$ or Au as the core and a phosphodiester moiety to form a prodrug of anti-cancer drugs. The anti-cancer drugs may be liberated in the presence of phosphodiesterase and may also possess magnetic tracking capability and good hydrophilicity. The nanoparticle delivery vehicle of the present invention may constitute a new class of candidates as anticancer drugs applicable in many types of cancer and would be promising in clinical development.

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. A phosphate-containing nanoparticle delivery vehicle of the formula:

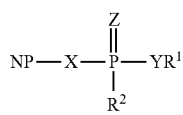

wherein NP is a nanoparticle;
  R¹ is an anticancer drug molecule selected from the group consisting of cytochalasin B, cytochalasin D, cytochalasin A, cytochalasin E, latrunculin, Phalloidin, actinomycin, doxorubicin, daunorubicin, valrubicin, idarubicin, 6-Mercaptopurine (6-MP), Azathioprine (AZA), Methotrexate, 6-thioguanine (6-TG), thioguanine, 6-thioinosine and thiouridine;
  R² is a member selected from the group consisting of OH, halogen, C1-C5 alkoxy group;
  each of X, Y is a member selected from the group consisting of NH, O and S; and
  Z is a member selected from the group consisting of O and S.

2. The phosphate-containing nanoparticle delivery vehicle as claimed in claim 1, wherein the nanoparticle is made of metal or metallic oxide.

3. The phosphate-containing nanoparticle delivery vehicle as claimed in claim 2, wherein the nanoparticle is made of a member selected from the group consisting of iron, cobalt, nickel and oxides thereof.

4. The phosphate-containing nanoparticle delivery vehicle as claimed in claim 2, wherein the nanoparticle is made of iron oxide or gold.

5. The phosphate-containing nanoparticle delivery vehicle as claimed in claim 1, wherein the nanoparticle is made of a member selected from the group consisting of titanium dioxide, zinc oxide, tin dioxide, copper, aluminum, cadmium selenide, silicon dioxide and diamond.

6. The phosphate-containing nanoparticle delivery vehicle as claimed in claim 1, wherein the nanoparticle further comprises a polyethylene glycol (PEG).

7. The phosphate-containing nanoparticle delivery vehicle as claimed in claim 1, wherein X is O.

8. The phosphate-containing nanoparticle delivery vehicle as claimed in claim 1, wherein Y is O.

9. The phosphate-containing nanoparticle delivery vehicle as claimed in claim 1, wherein Z is O.

10. The phosphate-containing nanoparticle delivery vehicle as claimed in claim 1, wherein R² is OH.

11. The phosphate-containing nanoparticle delivery vehicle as claimed in claim 1, wherein the actin inhibitor is a member selected from the group consisting of cytochalasin B, cytochalasin D, cytochalasin A, cytochalasin E, latrunculin and Phalloidin.

12. The phosphate-containing nanoparticle delivery vehicle as claimed in claim 1, wherein the cytotoxic antibiotic is a member selected from the group consisting of actinomycin, doxorubicin, daunorubicin, valrubicin and idarubicin.

13. The phosphate-containing nanoparticle delivery vehicle as claimed in claim 1, wherein the antimetabolite is a member selected from the group consisting of 6-Mercaptopurine (6-MP), Azathioprine (AZA), Methotrexate, 6-thioguanine (6-TG), thioguanine, 6-thioinosine and thiouridine.

* * * * *